United States Patent

Isobe et al.

Patent Number: 5,877,318
Date of Patent: Mar. 2, 1999

[54] HYDROQUINONE DERIVATIVE AND PHARMACEUTICAL USE THEREOF

[75] Inventors: Yoshiaki Isobe; Yuso Goto; Masanori Tobe; Osamu Takahashi, all of Saitama, Japan

[73] Assignee: Japan Energy Corporation, Tokyo, Japan

[21] Appl. No.: 113,826

[22] Filed: Jul. 10, 1998

Related U.S. Application Data

[62] Division of Ser. No. 933,208, Sep. 16, 1997, Pat. No. 5,821,247.

[30] Foreign Application Priority Data

Sep. 19, 1996 [JP] Japan .................... 8-248272/1996

[51] Int. Cl.$^6$ ................. C07D 239/545; C07D 405/12
[52] U.S. Cl. ............................. 544/310; 544/311
[58] Field of Search ..................... 544/310, 311

[56] References Cited

FOREIGN PATENT DOCUMENTS 0700908  3/1996  European Pat. Off. .

*Primary Examiner*—Mukund J. Shah
*Assistant Examiner*—Ann M. Kessinger
*Attorney, Agent, or Firm*—Fish & Richardson P.C.

[57] ABSTRACT

Disclosed is a hydroquinone derivative or a pharmaceutically acceptable salt thereof, the hydroquinone derivative being represented by formula (I):

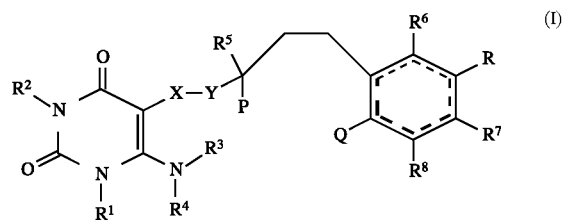

wherein $R^1$ is a phenyl group which is unsubstituted or substituted with a substituent or substituents each independently selected from the group consisting of a halogen atom, a C1–4 alkyl group and a C1–4 alkoxy group;

$R^2$ is a hydrogen atom or a C1–4 alkyl group;

each of $R^3$ and $R^4$ is independently a hydrogen atom or a C1–4 alkyl group;

$R^5$ is a hydrogen atom or a C1–4 alkyl group;

each of $R^6$, $R^7$ and $R^8$ is independently a hydrogen atom or a C1–4 alkyl group;

P is a hydroxyl group;

Q is a hydroxyl group, a C1–4 alkoxy group, a C1–18 acyloxy group or an oxo group;

P may form together with Q an ether bond;

R is a hydroxyl group, a C1–4 alkoxy group, a C1–18 acyloxy group or an oxo group, provided that when one of said Q and said R is an oxo group, the other is also an oxo group;

X is a single bond, an —NR$^{10}$— group or a —CH$_2$—NR$^{10}$— group in which R$^{10}$ is a hydrogen atom or a C1–4 alkyl group;

Y is a methylene group or a carbonyl group; and dotted bonds in a six membered ring represent that said six membered ring has the maximum number of double bonds.

2 Claims, No Drawings

HYDROQUINONE DERIVATIVE AND PHARMACEUTICAL USE THEREOF

This application is a division of application Ser. No. 08/933,208 filed Sep. 16, 1997 now U.S. Pat. No. 5,821,247.

BACKGROUND OF THE INVENTION

1. Field of the Invention

The present invention relates to a novel hydroquinone derivative useful for treating various allergic diseases and a pharmaceutical use thereof. More particularly, the present invention relates to a therapeutic agent for allergic diseases which contains the hydroquinone derivative as an active ingredient.

2. Description of the Prior Art

Allergic reactions which cause allergic diseases are generally classified into types I to IV. Particularly, the type IV reaction has been known to be dominant in atopic dermatitis, contact dermatitis, chronic bronchial asthma, psoriasis, graft-versus-host diseases, and so on. Effectiveness of antihistaminics and chemical mediator release inhibitors against these diseases is limited, and therefore steroids have been used for their therapy. In addition, cyclosporin and taclorims have also been known to be effective for suppression of graft rejection and therapy for graft-versus-host diseases developed after transplantation, and their application has been expanded into therapy for dermatitis [Lancet, 339, 1120 (1992); J. Invest. Dermatol, 98, 851 (1992), etc.]. However, such drugs are sometimes disadvantageous. Steroids cause undesirable side effects such as infectious diseases, atrophy of adrenal glands, osteoporosis, diabetes mellitus, and growth inhibition in children. For cyclosporin or taclorims, side effects caused by their immunosuppression effect, such as infectious diseases and diabetes mellitus, would be feared.

The applicant have proposed uracil derivatives which can inhibit type IV allergic reactions (see Japanese Patent Application Laid-open No. 8-109171 which corresponds to EP700908A1). However, development of more potent and safe drugs for treating allergic diseases, especially those responsible for type IV allergic reactions, is still required.

OBJECTS AND SUMMARY OF THE INVENTION

In these situations, the present invention is intended to solve the above mentioned problems. Therefore, the object of the present invention is to provide a novel compound and a therapeutic agent comprising the compound as an active ingredient which are useful for treating various allergic diseases, especially those responsible for type IV allergic reactions.

The inventors have made intensive and extensive studies with a view toward developing a therapeutic agent which is effective for treating various allergic diseases, especially those responsible for type IV allergic reactions. As a result, it has been found that a hydroquinone derivative having a 2,4 (1H, 3H)-pyrimidinedione ring therein markedly inhibits type IV allergic reactions. The present invention is completed.

Accordingly, the object of the present invention is to provide a hydroquinone derivative of formula (I) below or a pharmaceutically acceptable salt thereof and a pharmaceutical composition containing the hydroquinone derivative or pharmaceutically acceptable salt thereof as an active ingredient, especially for treatment of allergic diseases:

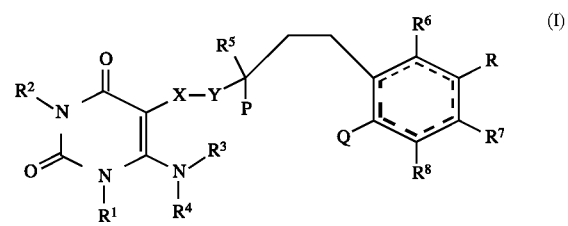

wherein:
- $R^1$ is a phenyl group which is unsubstituted or substituted with a substituent or substituents each independently selected from the group consisting of a halogen atom, a C1–4 alkyl group and a C1–4 alkoxy group;
- $R^2$ is a hydrogen atom or a C1–4 alkyl group;
- each of $R^3$ and $R^4$ is independently a hydrogen atom or a C1–4 alkyl group;
- $R^5$ is a hydrogen atom or a C1–4 alkyl group;
- each of $R^6$, $R^7$ and $R^8$ is independently a hydrogen atom or a C1–4 alkyl group;
- P is a hydroxyl group;
- Q is a hydroxyl group, a C1–4 alkoxy group, a C1–18 acyloxy group or an oxo group;
- P may form together with Q an ether bond;
- R is a hydroxyl group, a C1–4 alkoxy group, a C1–18 acyloxy group or an oxo group, provided that when either of the Q and the R is an oxo group, the other is also an oxo group;
- X is a single bond, an —$NR^{10}$— group or a —$CH_2$—$NR^{10}$— group in which $R^{10}$ is a hydrogen atom or a C1–4 alkyl group;
- Y is a methylene group or a carbonyl group; and
- dotted bonds in a six membered ring represent that the six membered ring has the maximum number of double bonds.

The hydroquinone derivative and pharmaceutically acceptable salt thereof of the present invention are concretely explained as follows.

The hydroquinone derivative of the present invention has an asymmetric carbon atom attached by $R^5$ and P as shown in formula (I), which leads two types of enantiomers depending on the steric configuration of $R^5$ and P on the asymmetric carbon atom. In the present invention, both of the enantiomers are included.

The hydroquinone derivative of the present invention contains a hydroquinone-related moiety represented by formula (II):

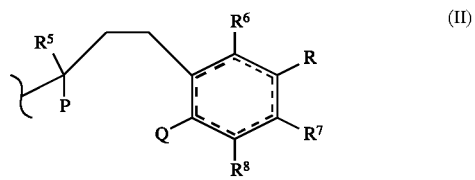

wherein P, Q, R, $R^5$, $R^6$, $R^7$ and $R^8$ are the same as defined for formula (I) above, and dotted bonds in a six membered ring represent that the six membered ring has the maximum number of double bonds.

The moiety of formula (II) has the following three types of variations depending on the P, Q, and R selected therein.

At first, when P forms together with Q an ether bond, the moiety of formula (II) has a chroman-type structure of formula (III):

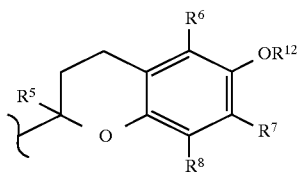

wherein $R^5$, $R^6$, $R^7$ and $R^8$ are the same as defined for formula (I) above; and $R^{12}$ is a hydrogen atom, a C1–4 alkyl group or a C1–18 acyl group.

At second, when P is a hydroxyl group and each of Q and R is independently a hydroxyl group, a C1–4 alkoxy group or a C1–18 acyloxy group, the moiety of formula (II) has a hydroquinone-type structure of formula (IV), which is a hydrated form of the above mentioned chroman-type structure (III):

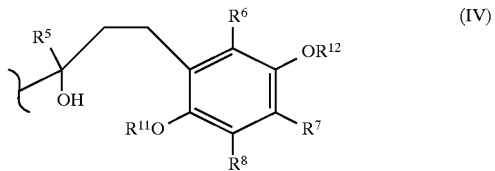

wherein $R^5$, $R^6$, $R^7$ and $R^8$ are the same as defined for formula (I); and each of $R^{11}$ and $R^{12}$ is independently a hydrogen atom, a C1–4 alkyl group or a C1–18 acyl group.

At last, when P is a hydroxyl group and both of Q and R are oxo groups, the moiety of formula (II) has a quinone-type structure of formula (V), which is an oxidized form of the above mentioned hydroquinone-type structure (IV):

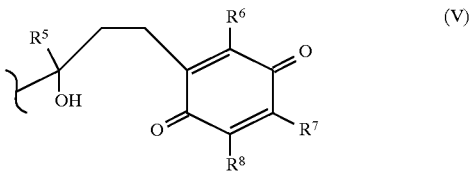

wherein $R^5$, $R^6$, $R^7$ and $R^8$ are the same as defined for formula (I) above.

In general, these three types of structures of the hydroquinone-related moiety closely relate to one another, and the interconversion between them is reversible [see, e.g., J. Org. Chem., 46, 2445 (1981)]. For example, with respect to the interconversion between the chroman-type structure (III) and the quinone-type structure (V), it has been known that α-tocopherol containing the structure of formula (III) (wherein $R^5$=$R^6$=$R^7$=$R^8$=$CH_3$, and $R^{12}$=H) as a partial moiety produces in vivo α-tocopherol quinone which has the structure of formula (V) therein as a partial moiety [see, e.g., J. Biol. Chem., 238, 2912 (1963)].

In formula (I), each of $R^2$, $R^3$, $R^4$, $R^5$, $R^6$, $R^7$, $R^8$ and $R^{10}$ is a hydrogen atom or a C1–4 alkyl group such as methyl group, ethyl group, propyl group, isopropyl group, butyl group, sec-butyl group, tert-butyl group and isobutyl group. Particularly preferred is a hydrogen atom or methyl group.

As the hydroquinone-related moiety of formula (II), which is a partial structure of the compound of formula (I) of the present invention, preferred are those in which each of $R^5$, $R^6$, $R^7$ and $R^8$ is a hydrogen atom or a methyl group. Specific examples of such moiety of formula (II) include: for the chroman-type structure of formula (III), 2-methyl-6-hydroxy-2-chromanyl group, 2,8-dimethyl-6-hydroxy-2-chromanyl group, 2,5,8-trimethyl6-hydroxy-2-chromanyl group, 2,7,8-trimethyl-6-hydroxy-2-chromanyl group and 2,5,7,8-tetramethyl-6-hydroxy-2-chromanyl group; for the hydroquinone-type structure of formula (IV),3-(2,5-dihydroxyphenyl)-1-hydroxy-1-metylpropyl group, 3-(2,5-dihydroxy-3-methylphenyl)-1-hydroxy-1-metylpropyl group, 3-(2,5-dihydroxy-3,6-dimethylphenyl)-1-hydroxy-1-metylpropyl group, 3-(2,5-dihydroxy-3,4-dimethylphenyl)-1-hydroxy-1-metylpropyl and 3-(2,5-dihydroxy-3,4,6-trimethylphenyl)-1-hydroxy-1-metylpropyl group; and for the quinone-type structure of formula (V), 3-(1,4-benzoquinon-2-yl)-1-hydroxy-1-metylpropyl group, 1-hydroxy-1-methyl-3-(6-methyl-1,4-benzoquinon-2-yl) propyl group, 3-(3,6-dimethyl-1,4-benzoquinon-2-yl)-1-hydroxy-1-metylpropyl group, 3-(5,6-dimethyl-1,4-benzoquinon-2-yl)-1-hydroxy-1-metylpropyl group and 1-hydroxy-1-methyl-3-(3,5,6-trimethyl-1,4-benzoquinon-2-yl)propyl group. Among them, especially preferred are 2,5,7,8-tetramethyl-6-hydroxy-2-chromanyl group, 3-(2,5-dihydroxy-3,4,6-trimethylphenyl)-1-hydroxy-1-metylpropyl group and 1-hydroxy-1-methyl-3-(3,5,6-trimethyl-1,4-benzoquinon-2-yl)propyl group.

A hydrogen atom of a phenolic hydroxyl group in a benzene ring of the chroman-type structure of formula (III) or the hydroquinone-type structure of formula (IV) may be replaced by a C1–4 alkyl group or a C1–18 acyl group. That is, in formula (III), $R^{12}$ is a hydrogen atom, a C1–4 alkyl group or a C1–18 acyl group, and more preferably a hydrogen atom or a C1–18 acyl group. In formula (IV), each of $R^{11}$ and $R^{12}$ is independently a hydrogen atom, a C1–4 alkyl group or a C1–18 acyl group, and more preferably a hydrogen atom or a C1–18 acyl group. When each of $R^{11}$ and $R^{12}$ is a hydrogen atom or an acyl groups, corresponding each of $OR^{11}$ and $OR^{12}$ becomes a hydroxyl group or a hydroxyl group protected with an acyl group. Specific examples of such acyl group include an alkanoyl group such as a formyl group, an acetyl group, a propionyl group, a butyryl group, a pentanoyl group, a hexanoyl group, an octanoyl group, a decanoyl group, a dodecanoyl group, a tetradecanoyl group, a hexadecanoyl group and an octadecanoyl group; and an acyl group containing an aromatic ring such as a benzoyl group, an anisoyl group (methoxybenzoyl group), a phenylacetyl group and a phenylpropionyl group.

In formula (I), $R^1$ at the 1-position of 2,4 (1H, 3H)-pyrimidinedione ring is a phenyl group unsubstituted or substituted with a substituent or substituents each independently selected from the group consisting of a halogen atom, a C1–4 alkyl group and a C1–4 alkoxy group. The halogen atom used herein is fluorine, chlorine, bromine or iodine, and preferably fluorine, chlorine or bromine. The C1–4 alkyl group is a linear or branched alkyl group, such as a methyl group, an ethyl group, a propyl group, an isopropyl group, a butyl group, a sec-butyl group, a tert-butyl group or an isobutyl group. The C1–4 alkoxy group is an alkyl-oxy group comprising the alkyl group. The substituted phenyl group of $R^1$ is exemplified as follows.

Specific examples of the phenyl group substituted with a halogen atom or halogen atoms (e.g., fluorine, chlorine and bromine) include 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2,3-difluorophenyl, 2,4-difluorophenyl, 2,5-difluorophenyl, 2,6-difluorophenyl, 3,4-difluorophenyl, 3,5-difluorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,4-dibromophenyl, 2,5-dibromophenyl, 2,6-dibromophenyl, 2-chloro-4-fluorophenyl, 3-chloro-4-fluorophenyl, 4-chloro-2-fluorophenyl, 4-bromo-2-chlorophenyl, 2,3,4-trifluorophenyl, 2,3,6-trifluorophenyl, 2,4,5-trifluorophenyl, 2,4,6-trifluorophenyl, 2,3,4-trichlorophenyl, 2,4,5- trichlorophenyl, 2,4,6-trichlorophenyl, and 3,4,5-trichlorophenyl groups.

Specific examples of the phenyl group substituted with a C1–4 alkyl group or C1–4 alkyl groups include 2-methylphenyl, 3-methylphenyl, 4-methylphenyl, 2-ethylphenyl, 3-ethylphenyl, 4-ethylphenyl, 2-propylphenyl, 4-propylphenyl, 2-tert-butylphenyl, 4-butylphenyl, 4-tert-butylphenyl, 4-sec-butylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,6-diethylphenyl, 2,5-di-tert-butylphenyl, 3,5-di-tert-butylphenyl and 2,4,6-trimethylphenyl groups.

Specific examples of the phenyl group substituted with a C1–4 alkoxy group or C1–4 alkoxy groups include 2-methoxyphenyl, 3-methoxyphenyl, 4-methoxyphenyl, 2-ethoxyphenyl, 3-ethoxyphenyl, or 4-ethoxyphenyl group.

The phenyl group of $R^1$ in formula (I) may be substituted with a plurality of deferent types of substituents. Specific examples of such substituted phenyl group include 2-fluoro-4-methylphenyl, 2-fluoro-5-methylphenyl, 3-fluoro-2-methylphenyl, 3-fluoro-4-methylphenyl, 4-fluoro-2-methylphenyl, 5-fluoro-2-methylphenyl, 2-chloro-4-methylphenyl, 2-chloro-5-methylphenyl, 2-chloro-6-methylphenyl, 3-chloro-2-methylphenyl, 3-chloro-4-methylphenyl, 2-bromo-4-methylphenyl, 3-bromo-4-methylphenyl, 4-bromo-2-methylphenyl, 4-bromo-3-methylphenyl, 3-fluoro-2-methoxyphenyl, 3-fluoro-4-methoxyphenyl, 3-chloro-4-methoxyphenyl, 5-chloro-2-methoxyphenyl, 2-chloro-5-methoxyphenyl, 2-methoxy-5-methylphenyl, 2-methoxy-6-methylphenyl, 4-methoxy-2-methylphenyl and 5-methoxy-2-methylphenyl groups.

In formula (I), $R^2$ at the 3-position of 2,4 (1H, 3H)-pyrimidinedione ring is a hydrogen atom or a C1–4 alkyl group, and preferably a hydrogen atom or a methyl group. Each of $R^3$ and $R^4$ in $NR^3R^4$ at the 6-position of 2,4 (1H, 3H)-pyrimidinedione ring in formula (I) is also a hydrogen atom or a C1–4 alkyl group, and preferably a hydrogen atom or a methyl group.

In the compound of formula (I), one containing the chroman moiety of formula (III) has a basic structure in which a 2,4 (1H, 3H)-pyrimidinedione ring is connected to the chroman ring through a —X—Y— group. Examples of such basic structure include those in which X is an —$NR^{10}$— group and Y is a carbonyl group, such as 5-(chroman-2-carboxamido)-2,4 (1H, 3H)-pyrimidinedione, 5-(N-methylchroman-2-carboxamido)-2,4 (1H, 3H)-pyrimidinedione, 5-(N-ethylchroman-2-carboxamido)-2,4 (1H, 3H)-pyrimidinedione, 5-(N-propylchroman-2-carboxamido)-2,4 (1H, 3H)-pyrimidinedione and 5-(N-butylchroman-2-carboxamido)-2,4 (1H, 3H)-pyrimidinedione; those in which X is an —$NR^{10}$— group and Y is a methylene group, such as 5-[N-(2-chromanylmethyl)amino]-2,4 (1H, 3H)-pyrimidinedione, 5-[N-(2-chromanylmethyl)-N-methylamino]-2,4 (1H, 3H)-pyrimidinedione, 5-[N-(2-chromanylmethyl)-N-ethylamino]-2,4 (1H, 3H)-pyrimidinedione, 5-[N-(2-chromanylmethyl)-N-propylamino]-2,4 (1H, 3H)-pyrimidinedione and 5-[N-butyl-N-(2-chromanylmethyl) amino]-2,4 (1H, 3H)-pyrimidinedione; those in which X is a single bond and Y is a methylene group or a carbonyl group, such as 5-(2-chromanylmethyl)-2,4 (1H, 3H)-pyrimidinedione and 5-(2-chromancarbonyl)-2,4 (1H, 3H)-pyrimidinedione; those in which X is —$CH_2$—$NR^{10}$— group and Y is a methylene group, such as 5-[N-(2-chromanylmethyl)aminomethyl]-2,4 (1H, 3H)-pyrimidinedione, 5-[N-(2-chromanylmethyl)-N-methylaminomethyl]-2,4 (1H, 3H)-pyrimidinedione,5-[N-(2-chromanylmethyl)-N-ethylaminomethyl]-2,4 (1H, 3H)-pyrimidinedione, 5-[N-(2-chromanylmethyl)-N-propylaminomethyl]-2,4 (1H, 3H)-pyrimidinedione and 5-[N-butyl-N-(2-chromanylmethyl)aminomethyl]-2,4 (1H, 3H)-pyrimidinedione; and those in which X is a —$CH_2$—$NR^{10}$— group and Y is a carbonyl group, such as 5-(chroman-2-carboxamidomethyl)-2,4 (1H, 3H)-pyrimidinedione, 5-(N-methylchroman-2-carboxamidomethyl)-2,4 (1H, 3H)-pyrimidinedione, 5-(N-ethylchroman-2-carboxamidomethyl)-2,4 (1H, 3H)-pyrimidinedione, 5-(N-propylchroman-2-carboxamidomethyl)-2,4 (1H, 3H)-pyrimidinedione and 5-(N-butylchroman-2-carboxamidomethyl)-2,4 (1H, 3H)-pyrimidinedione. These basic structures have the above mentioned $R^1$, $R^2$, and $NR^3R^4$ at the 1-, 3- and 6-positions of the 2,4 (1H, 3H)-pyrimidinedione ring, respectively; and also have $R^5$, $R^6$, $OR^{12}$, $R^7$ and $R^8$ at the 2-, 5-, 6-, 7- and 8-positions of the chroman ring, respectively.

In the compound of formula (I), one containing the hydroquinone moiety of formula (IV) has a basic structure having a 3-phenylpropyl group instead of the 2-chromanyl group in the above mentioned chroman ring-containing basic structure. The 3-phenylpropyl group has a hydroxyl group and $R^5$ at the 1-position of the propyl moiety thereof, and also has $OR^{11}$, $R^8$, $R^7$, $OR^{12}$ and $R^6$ at the 2-, 3-, 4-, 5- and 6-positions of the phenyl moiety thereof, respectively.

In the compound of formula (I), one containing the quinone moiety of formula (V) has a basic structure having a 3-(1,4-benzoquinon-2-yl)propyl group instead of the 2-chromanyl group in the above mentioned chroman ring-containing basic structure. The 3-(1,4-benzoquinon-2-yl) propyl group has a hydroxyl group and $R^5$ at the 1-position of the propyl moiety thereof, and also has $R^6$, $R^7$, and $R^8$ at the 3-, 5- and 6-positions of the benzoquinone moiety thereof, respectively.

Proper selection of the substituents of the 2,4 (1H, 3H)-pyrimidinedione ring and the hydroquinone-related moiety of formula (II) can afford preferable hydroquinone derivative of the present invention. That is, selection of a hydrogen atom or a methyl group for $R^2$, $R^3$, and $R^4$ on the 2,4 (1H, 3H)-pyrimidinedione ring; $R^5$, $R^6$, $R^7$, and $R^8$ on the moiety of formula (II); and $R^{10}$ in —X—Y—affords the more preferable compound of formula (I). Selection of a methyl for all of $R^5$, $R^6$, $R^7$, and $R^8$ affords the particularly more preferable compound of formula (I).

Specific examples of such particularly preferable hydroquinone derivative of formula (I) of the present invention include:

for those which have the chroman moiety of formula (III) therein, 6-amino-5-(6-hydroxy-2,5,7,8-tetramethylchroman-2-carboxamido)-3-methyl-1-phenyl-2,4 (1H, 3H)-pyrimidinedione, 6-amino-1-(4-fluorophenyl)-5-(6-hydroxy-2,5,7,8-tetramethylchroman-2-carboxamido)-3-methyl-2,4 (1H, 3H)-pyrimidinedione, 6-amino-1-(4-chlorophenyl)-5- 6-hydroxy-2,5,7,8-tetramethylchroman-2-carboxamido)-3-methyl-2,4 (1H, 3H)-pyrimidinedione, 6-amino-1-(2-chlorophenyl)-5-(6-hydroxy-2,5,7,8-tetramethylchroman-2-carboxamido)-3-methyl-2,4 (1H, 3H)-pyrimidinedione, 6-amino-1-(3-chlorophenyl)-5-(6-hydroxy-2,5,7,8-tetramethylchroman-2-carboxamido)-3-methyl-2,4 (1H, 3H)-pyrimidinedione, 6-amino-5-(6-hydroxy-2,5,7,8-tetramethylchroman-2-carboxamido)-3-methyl-1-(4-methylphenyl)-2,4 (1H, 3H)-pyrimidinedione, 6-amino-5-(6-hydroxy-2,5,7,8-tetramethylchroman-2-carboxamido)-1-(4-methoxyphenyl)-3-methyl-2,4 (1H, 3H)-pyrimidinedione, 5-(6-hydroxy-2,5,7,8-tetramethylchroman-2-carboxamido)-3-methyl-6-methylamino-1-phenyl-2,4 (1H, 3H)-pyrimidinedione, 6-dimethylamino-1-(4-fluorophenyl)-5-(6-hydroxy-2,5,7,8-tetramethylchroman-2-carboxamido)-3-methyl-2,4 (1H, 3H)-pyrimidinedione, 5-(6-acetoxy-2,5,7,8-tetramethylchroman-2-carboxamido)-6-amino-3-methyl-1-phenyl-2,4 (1H, 3H)-pyrimidinedione, 6-amino-5-[(6-hydroxy-2,5,7,8-tetramethyl-2-chromanylmethyl)amino]-3-methyl-1-phenyl-2,4 (1H, 3H)-pyrimidinedione, 6-amino-5-(6-hydroxy-2,5,7,8-tetramethyl-2-chromanylmethyl)-3-methyl-1-phenyl-2,4 (1H, 3H)-pyrimidinedione, 6-amino-5-(6-hydroxy-2,5,7,8-tetramethyl-2-chromancarbonyl)-3-methyl-1-phenyl-2,4 (1H, 3H)-pyrimidinedione, 6-amino-5-[N-(6-hydroxy-2,5,7,8-tetramethyl-2-chromanylmethyl)aminomethyl]-3-methyl-1-phenyl-2,4 (1H, 3H)-pyrimidinedione, 6-amino-5-(6-hydroxy-2,5,7,8-tetramethylchroman-2-carboxamidomethyl)-3-methyl-1-phenyl-2,4 (1H, 3H)-pyrimidinedione, and 6-amino-3-methyl-5-(N-methyl-6-hydroxy-2,5,7,8-tetramethylchroman-2-carboxamidomethyl)-1-phenyl-2,4 (1H, 3H)-pyrimidinedione;

for those which have the hydroquinone moiety of formula (IV) therein, 6-amino-5-[4-(2,5-diacetoxy-3,4,6-trimethylphenyl)-2-hydroxy-2-methylbutyramido]-3-methyl-1-phenyl-2,4 (1H, 3H)-pyrimidinedione, 6-amino-5-[4-(2,5-diacetoxy-3,4,6-trimethylphenyl)-2-hydroxy-2-methylbutyramido]-1-(4-fluorophenyl)-3-methyl-2,4 (1H, 3H)-pyrimidinedione, 6-amino-1-(4-chlorophenyl)-5-[4-(2,5-diacetoxy-3,4,6-trimethylphenyl)-2-hydroxy-2-methylbutyramido]-3-methyl-2,4 (1H, 3H)-pyrimidinedione, 6-amino-1-(2-chlorophenyl)-5-[4-(2,5-diacetoxy-3,4,6-trimethylphenyl)-2-hydroxy-2-methylbutyramido]-3-methyl-2,4 (1H, 3H)-pyrimidinedione, 6-amino-1-(3-chlorophenyl)-5-[4-(2,5-diacetoxy-3,4,6-trimethylphenyl)-2-hydroxy-2-methylbutyramido]-3-methyl-2,4 (1H, 3H)-pyrimidinedione, 6-amino-5-[4-(2,5-diacetoxy-3,4,6-trimethylphenyl)-2-hydroxy-2-methylbutyramido]-3-methyl-1-(4-methylphenyl)-2,4 (1H, 3H)-pyrimidinedione, 6-amino-5-[4-(2,5-diacetoxy-3,4,6-trimethylphenyl)-2-hydroxy-2-methylbutyramido]-1-(4-methoxyphenyl)-3-methyl-2,4 (1H, 3H)-pyrimidinedione, 5-[4-(2,5-diacetoxy-3,4,6-trimethylphenyl)-2-hydroxy-2-methylbutyramido]-3-methyl-6-methylamino-1-phenyl-2,4 (1H, 3H)-pyrimidinedione, 5-[4-(2,5-diacetoxy-3,4,6-trimethylphenyl)-2-hydroxy-2-methylbutyramido]-6-dimethylamino-1-(4-fluorophenyl)-3-methyl-2,4 (1H, 3H)-pyrimidinedione, 6-amino-5-[4-(2,5-dihydroxy-3,4,6-trimethylphenyl)-2-hydroxy-2-methylbutyramido]-3-methyl-1-phenyl-2,4 (1H, 3H)-pyrimidinedione, 6-amino-5-[[4-(2,5-diacetoxy-3,4,6-trimethylphenyl)-2-hydroxy-2-methylbutyl]amino]-3-methyl-1-phenyl-2,4 (1H, 3H)-pyrimidinedione, 6-amino-5-[4-(2,5-diacetoxy-3,4,6-trimethylphenyl)-2-hydroxy-2-methylbutyl]-3-methyl-1-phenyl-2,4 (1H, 3H)-pyrimidinedione, 6-amino-5-[4-(2,5-diacetoxy-3,4,6-trimethylphenyl)-2-hydroxy-2-methylbutyryl]-3-methyl-1-phenyl-2,4 (1H, 3H)-pyrimidinedione, 6-amino-5-[N-[4-(2,5-diacetoxy-3,4,6-trimethylphenyl)-2-hydroxy-2-methylbutyl]aminomethyl]-3-methyl-1-phenyl-2,4 (1H, 3H)-pyrimidinedione, and 6-amino-5-[4-(2,5-diacetoxy-3,4,6-trimethylphenyl)-2-hydroxy-2-methylbutyramidomethyl]-3-methyl-1-phenyl-2,4 (1H, 3H)-pyrimidinedione;

for those which have the quinone moiety of formula (V) therein, 6-amino-3-methyl-1-phenyl-5-[4-(3,5,6-trimethyl-1,4-benzoquinon-2-yl)-2-hydroxy-2-methylbutyramido]-2,4 (1H, 3H)-pyrimidinedione, 6-amino-1-(4-fluorophenyl)-3-methyl-5-[4-(3,5,6-trimethyl-1,4-benzoquinon-2-yl)-2-hydroxy-2-methylbutyramido]-2,4 (1H, 3H)-pyrimidinedione, 6-amino-1-(4-chlorophenyl)-3-methyl-5-[4-(3,5,6-trimethyl-1,4-benzoquinon-2-yl)-2-hydroxy-2-methylbutyramido]-2,4 (1H, 3H)-pyrimidinedione, 6-amino-1-(2-chlorophenyl)-3-methyl-5-[4-(3,5,6-trimethyl-1,4-benzoquinon-2-yl)-2-hydroxy-2-methylbutyramido]-2,4 (1H, 3H)-pyrimidinedione, 6-amino-1-(3-chlorophenyl)-3-methyl-5-[4-(3,5,6-trimethyl-1,4-benzoquinon-2-yl)-2-hydroxy-2-methylbutyramido]-2,4 (1H, 3H)-pyrimidinedione, 6-amino-3-methyl-1-(4-methylphenyl)-5-[4-(3,5,6-trimethyl-1,4-benzoquinon-2-yl)-2-hydroxy-2-methylbutyramido]-2,4 (1H, 3H)-pyrimidinedione, 6-amino-1-(4-methoxyphenyl)-3-methyl-5-[4-(3,5,6-trimethyl-1,4-benzoquinon-2-yl)-2-hydroxy-2-methylbutyramido]-2,4 (1H, 3H)-pyrimidinedione, 3-methyl-6-methylamino-1-phenyl-5-[4-(3,5,6-trimethyl-1,4-benzoquinon-2-yl)-2-hydroxy-2-methylbutyramido]-2,4 (1H, 3H)-pyrimidinedione, 6-dimethylamino-1-(4-fluorophenyl)-3-methyl-5-[4-(3,5,6-trimethyl-1,4-benzoquinon-2-yl)-2-hydroxy-2-methylbutyramido]-2,4 (1H, 3H)-pyrimidinedione, 6-amino-3-methyl-1-phenyl-5-[[4-(3,5,6-trimethyl-1,4-benzoquinon-2-yl)-2-hydroxy-2-methylbutyl]amino]-2,4 (1H, 3H)-pyrimidinedione, 6-amino-3-methyl-1-phenyl-5-[4-(3,5,6-trimethyl-1,4-benzoquinon-2-yl)-2-hydroxy-2-methylbutyl]-2,4 (1H, 3H)-pyrimidinedione, 6-amino-3-methyl-1-phenyl-5-[4-(3,5,6-trimethyl-1,4-benzoquinon-2-yl)-2-hydroxy-2-methylbutyryl]-2,4 (1H, 3H)-pyrimidinedione, 6-amino-3-methyl-1-phenyl-5-[N-[4-(3,5,6-trimethyl-1,4-benzoquinon-2-yl)-2-hydroxy-2-methylbutyl]aminomethyl]-2,4 (1H, 3H)-pyrimidinedione, 6-amino-3-methyl-1-phenyl-5-[4-(3,5,6-trimethyl-1,4-benzoquinon-2-yl)-2-hydroxy-2-methylbutyramidomethyl]-2,4 (1H, 3H)-pyrimidinedione;

and pharmaceutically acceptable salts thereof. Here, the term "a pharmaceutically acceptable salt" means a sodium, potassium, calcium, ammonium, hydrochloride, sulfate, acetate or succinate salt of any of the hydroquinone derivatives which have a dissociating (i.e., salt-forming) functional group.

The hydroquinone derivative of formula (I) of the present invention can generally be prepared by synthesizing an intermediate corresponding to the 2,4 (1H, 3H)-pyrimidinedione moiety and an intermediate corresponding to the moiety of formula (II) separately and then coupling both of the intermediates to each other under an appropriate reaction condition. The intermediate corresponding to the 2,4 (1H, 3H)-pyrimidinedione moiety, 6-amino-2,4 (1H, 3H)-pyrimidinedione, can be prepared, for example, by the method disclosed in Japanese Patent Application Laid-open No. 8-109171 (corresponding to EP 700908A1). With respect to the intermediate corresponding to the moiety of formula (II), an intermediate corresponding to the chroman-type structure of formula (III) can be synthesized, for example, by the method disclosed in U.S. Pat. No. 4,026,907; and an intermediate corresponding to the hydroquinone-type structure of formula (IV) or the quinone-type structure of formula (V) can be synthesized, for example, by the method described in *J. Org. Chem.*, 46, 2445 (1981).

The hydroquinone derivative of formula (I) of the present invention may also be prepared in the following various ways depending on the types of the —X—Y— groups therein.

For example, a hydroquinone derivative of formula (I) in which —X—Y— is —NH—CO— may be prepared by introducing a nitroso or nitro group into a 6-amino-2,4 (1H, 3H)-pyrimidinedione derivative, reducing the resultant to obtain a 5,6-diamino-2,4 (1H, 3H)-pyrimidinedione derivative, and then condensing it with a carboxylic acid corresponding to any of formulae (III), (IV) and (V). The condensation process can be performed, for example, by a conventional method used for peptide synthesis such as a mixed anhydride method, an acid halide method, an activated ester method and a carbodiimide method.

A hydroquinone derivative of formula (I) in which —X—Y— is —NR$^{10}$—CH$_2$— may be prepared from a 5,6-diamino-2,4 (1H, 3H)-pyrimidinedione derivative and an aldehyde corresponding to formula (III), (IV) or (V) through reductive amination. It may also be prepared by reducing the above mentioned hydroquinone derivative of formula (I) in which —X—Y— is —NR$^{10}$—CO—.

A hydroquinone derivative of formula (I) in which —X—Y— is —CH$_2$—NR$^{10}$—CO— may be prepared, for example, through Mannich aminomethylation of the 6-amino-2,4 (1H, 3H)-pyrimidinedione derivative into a 6-amino-5-(aminomethyl)-2,4 (1H, 3H)-pyrimidinedione derivative, followed by condensation with a carboxylic acid corresponding to formula (III), (IV) or (V). The 6-amino-5-(aminomethyl)-2,4 (1H, 3H)-pyrimidinedione derivative may also be prepared from the 6-amino-2,4 (1H, 3H)-pyrimidinedione derivative through Sandmeyer formylation followed by reductive amination.

A hydroquinone derivative of formula (I) in which —X—Y— is —CH$_2$—NR$^{10}$—CH$_2$— may be prepared, for example, from the 6-amino-5-aminomethyl-2,4 (1H, 3H)-pyrimidinedione derivative and an aldehyde corresponding to formula (III), (IV) or (V) through reductive amination thereof. It may also be prepared by reducing the above mentioned hydroquinone derivative of formula (I) in which —X—Y— is —CH$_2$—NR$^{10}$—CO—.

A hydroquinone derivative of formula (I) in which —X—Y— is —CH$_2$— may be prepared from the 6-amino-2,4 (1H, 3H)-pyrimidinedione derivative and a chloromethyl derivative corresponding to formula (III), (IV) or (V).

A hydroquinone derivative of formula (I) in which —X—Y— is —CO— may be prepared from the 6-amino-2,4 (1H, 3H)-pyrimidinedione derivative and a carboxylic acid corresponding to formula (III), (IV) or (V) through Friedel-Crafts acylation.

In the preparation of the hydroquinone derivative of formula (I) of the present invention, after the coupling of a 2,4(1H, 3H)-pyrimidinedione moiety with a hydroquinone-related moiety of any of formulae (III), (IV) and (V), interconversion between the chroman-, hydroquinone- and quinone-type moieties in the resultant coupled compound may be performed.

Reaction conditions for the above mentioned process may be suitably selected depending on the types of the reaction or the reagents employed. In general, conditions commonly employed for those reactions can be used. If necessary, a process for introduction or elimination of protecting groups may additionally be employed.

The pharmaceutical composition of the present invention, which is concretely a therapeutic agent for allergic diseases, contains the above mentioned hydroquinone derivative of formula (I) or pharmaceutically acceptable salt thereof as an active ingredient. The pharmaceutical composition can be used in various forms, such as an external preparation (ointment, cream, etc.), an oral preparation (tablets, capsules, powder, etc.), inhalant, injection, and so on. For example, for the preparation of an ointment, the hydroquinone derivative or pharmaceutically acceptable salts thereof of the present invention may be mixed into an ointment base such as vaseline, and optionally additives such as an absorption accelerator may be added thereto. For the preparation of tablets, the hydroquinone derivative or pharmaceutically acceptable salt thereof of the present invention may be mixed with excipients (lactose and starch, etc.), lubricants (talk, magnesium stearate, etc.), and other additives.

Dose of the therapeutic agent for allergic diseases of the present invention should be suitably selected depending on sex, age, body weight, disease type and condition of the patient to be treated. For example, for a patient suffered from atopic dermatitis, contact dermatitis, psoriasis, or the like, an ointment containing 0.01 to 10% of the active ingredient may be applied once or several times a day on the diseased portion of the patient. For a patient suffered from any of the above mentioned dermatitises, bronchial asthma, irritable pneumonia, graft rejection caused after transplantation, graft-versus-host diseases, or autoimmune diseases, for example, 0.01 to 100 mg/kg/day of dose in a male adult may be orally administered once a day or divided into several times a day as tablets, capsules or powder.

The hydroquinone derivative or a pharmaceutically acceptable salt thereof according to the present invention exhibits a markedly effective inhibitory action against allergic inflammations, especially those caused by type IV allergic reactions. Accordingly, the hydroquinone derivative or pharmaceutically acceptable salt thereof of the present invention is useful as a therapeutic agent for allergic diseases, especially those caused by type IV allergic reaction. In addition, it can be effectively absorbed through skin by percutaneous administration, and therefore is useful for treatment of various skin diseases such as atopic dermatitis, contact dermatitis and psoriasis. It can also be effectively absorbed through the digestive tract by oral administration, and therefore is useful for treatment of dermatitis covering a wide area, bronchial asthma, irritable pneumonia, graft rejection developed after transplantation, graft-versus-host diseases, autoimmune diseases, and so on. The hydroquinone derivative or pharmaceutically acceptable salt thereof is a non-steroidal material, and therefore advantageously exhibits no steroid-like side effect.

DESCRIPTION OF THE PREFERRED EMBODIMENTS

The present invention will be described in more detail with reference to the following examples.

EXAMPLE 1

6-Amino-5-(6-hydroxy-2 5,7,8-tetramethylchroman-2-carboxamido)-3-methyl-1-phenyl-2,4 (1H, 3H)-pyrimidinedione A mixture of 5,6-diamino-3-methyl-1-phenyl-2,4 (1H, 3H)-pyrimidinedione (3.02 g, 13 mmol), 6-hydroxy-2,5,7, 8-tetramethylchroman-2-carboxylic acid (3.58 g, 14.3 mmol) and 4-(dimethylamino)pyridine (0.32 g, 2.6 mmol) was suspended in dichloromethane (60 mL). To the resultant suspension was added dropwise a solution of N,N'-dicyclohexylcarbodiimide (2.82 g, 13.7 mmol) in dichloromethane (60 mL) at room temperature. The reaction mixture was stirred overnight and then filtered. The filtrate was concentrated and then subjected to silica-gel column chromatography, thereby giving the title compound (yield 57%).

TOF-MS (Time-of-flight type mass spectrum): m/z 465 [M+H]$^+$ $^1$H-NMR (CDCl$_3$): δ1.60 (3H, s), 1.90–2.04 (1H, m), 2.08 (3H, s), 2.18 (3H, s), 2.29 (3H, s), 2.30–2.38 (1H, m), 2.54–2.64 (2H, m), 3.34 (3H, s), 4.32 (1H, s), 5.17 (2H, bs), 7.27–7.36 (2H, m), 7.53–7.60 (3H, m), 8.41 (1H, bs)

EXAMPLE 2

6-Amino-5-(6-hydroxy-2,5,7,8-tetramethylchroman-2(R)-carboxamido)-3-methyl-1-phenyl-2,4 (1H, 3H)-Pyrimidinedione The title compound was prepared by repeating substantially the same procedure as Example 1, except using (R)-6-hydroxy-2,5,7,8-tetramethylchroman-2-carboxylic acid as the intermediate having a chroman-type structure. The data of $^1$H-NMR of the compound was compatible with those of the corresponding racemate obtained in Example 1.

[α]$_D$+59° (c=2, CHCl$_3$)

EXAMPLE 3

6-Amino-5-(6-hydroxy-2,5,7,8-tetramethylchroman-2(S)-carboxamido)-3-methyl-1-phenyl-2,4 (1H, 3H)-pyrimidinedione The title compound was prepared by repeating substantially the same procedure as Example 1, except using (S)-6-hydroxy-2,5,7,8-tetramethylchroman-2-carboxylic acid as the intermediate having chroman-type structure. The data of $^1$H-NMR of the compound was compatible with those of the corresponding racemate obtained in Example 1.

[α]$_D$−59° (c=2, CHCl$_3$)

EXAMPLE 4

6-Amino-1-(4-fluorophenyl)-5-(6-hydroxy-2,5,7,8-tetramethylchroman-2-carboxamido)-3-methyl-2,4 (1H, 3H)-pyrimidinedione The title compound was prepared by repeating substantially the same procedure as Example 1, except using 5,6-diamino-1-(4-fluorophenyl)-3-methyl-2,4 (1H, 3H)-pyrimidinedione.

TOF-MS: m/z 483 [M+H]$^+$ $^1$H-NMR (CDCl$_3$): δ1.60 (3H, s), 1.90–2.05 (1H, m), 2.08 (3H, s), 2.17 (3H, s), 2.28 (3H, s), 2.30–2.40 (1H, m), 2.54–2.64 (2H, m), 3.35 (3H, s), 4.33 (1H, s), 5.15 (2H, bs), 7.30–7.43 (4H, m), 8.43 (1H, bs)

EXAMPLE 5

6-Amino-1-(4-chlorophenyl)-5-(6-hydroxy-2 5,7,8-tetramethylchroman-2-carboxamido)-3-methyl-2,4 (1H, 3H)-pyrimidinedione The title compound was prepared by repeating substantially the same procedure as Example 1, except using 5,6-diamino-1-(4-chlorophenyl)-3-methyl-2,4 (1H, 3H)-pyrimidinedione.

TOF-MS: m/z 499 [M+H]$^+$ $^1$H-NMR (CDCl$_3$): δ1.60 (3H, s), 1.90–2.05 (1H, m), 2.07 (3H, s), 2.18 (3H, s), 2.29 (3H, s), 2.30–2.40 (1H, m), 2.55–2.65 (2H, m), 3.34 (3H, s), 4.31 (1H, s), 5.16 (2H, bs), 7.31 (2H, d, 8.4 Hz), 7.53 (2H, d, 8.4 Hz), 8.40 (1H, bs)

EXAMPLE 6

6-Amino-1-(2-chlorophenyl) -5-(6-hydroxy-2,5,7,8-tetramethylchroman-2-carboxamido)-3-methyl-2,4 (1H, 3H)-pyrimidinedione The title compound was prepared by repeating substantially the same procedure as Example 1, except using 5,6-diamino-1-(2-chlorophenyl) -3-methyl-2,4 (1H, 3H)-pyrimidinedione.

TOF-MS: m/z 499 [M+H]$^+$ $^1$H-NMR (CDCl$_3$): δ1.61 (3H, s), 1.90–2.05 (1H, m), 2.09 (3H, s), 2.19 (3H, s), 2.29 (3H, s), 2.30–2.40 (1H, m), 2.54–2.64 (2H, m), 3.35 (3H, s), 4.30 (1H, s), 5.19 (2H, bs), 7.40–7.55 (3H, m), 7.55–7.65 (1H, m), 8.40 (1H, bs)

EXAMPLE 7

6-Amino-1-(3-chlorophenyl)-5-(6-hydroxy-2,5,7,8-tetramethylchroman-2-carboxamido)-3-methyl-2,4 (1H, 3H -pyrimidinedione The title compound was prepared by repeating substantially the same procedure as Example 1, except using 5,6-diamino-1-(3-chlorophenyl)-3-methyl-2,4 (1H, 3H)-pyrimidinedione.

TOF-MS: m/z 499 [M+H]$^+$ $^1$H-NMR (CDCl$_3$): δ1.60 (3H, s), 1.90–2.04 (1H, m), 2.08 (3H, s), 2.18 (3H, s), 2.29 (3H, s), 2.30–2.38 (1H, m), 2.54–2.64 (2H, m), 3.34 (3H, s), 4.32 (1H, s), 5.17 (2H, bs), 7.38–7.65 (4H, m), 8.43 (1H, bs)

EXAMPLE 8

6-Amino-5-(6-hydroxy-2,5,7,8-tetramethylchroman-2-carboxamido)-3-methyl-1-(4-methylphenyl)-2,4 (1H, 3H)-pyrimidinedione The title compound was prepared by repeating substantially the same procedure as Example 1, except using 5,6-diamino-3-methyl-1-(4-methylphenyl)-2,4 (1H, 3H)-pyrimidinedione.

TOF-MS: m/z 479 [M+H]$^+$ $^1$H-NMR (CDCl$_3$): δ1.60 (3H, s), 1.90–2.04 (1H, m), 2.08 (3H, s), 2.18 (3H, s), 2.29 (3H, s), 2.30–2.38 (1H, m), 2.39 (3H, s), 2.54–2.64 (2H, m), 3.34 (3H, s), 4.33 (1H, s), 5.18 (2H, bs), 7.20 (2H, d, 8.5 Hz), 7.34 (2H, d, 8.5 Hz), 8.40 (1H, bs)

EXAMPLE 9

6-Amino-5-(6-hydroxy-2,5,7,8-tetramethylchroman-2-carboxamido)-1-(4-methoxyphenyl) -3-methyl-2,4 (1H, 3H)-pyrimidinedione The title compound was prepared by repeating substantially the same procedure as Example 1, except using 5,6-diamino-1-(4-methoxyphenyl)-3-methyl-2,4 (1H, 3H)-pyrimidinedione.

TOF-MS: m/z 495 [M+H]$^+$

¹H-NMR (CDCl₃): δ1.60 (3H, s), 1.90–2.05 (1H, m), 2.10 (3H, s), 2.19 (3H, s), 2.29 (3H, s), 2.30–2.40 (1H, m), 2.55–2.65 (2H, m), 3.35 (3H, s), 3.87 (3H, s), 4.34 (1H, s), 5.16 (2H, bs), 7.06 (2H, d, 9.0 Hz), 7.25 (2H, d, 9.0 Hz), 8.40 (1H, bs)

EXAMPLE 10

6-Amino-5-(6-hydroxy-2,5,7,8-tetramethylchroman-2-carboxamido1)-phenyl-3-propyl-2,4 (1H, 3H)-pyrimidinedione The title compound was prepared by repeating substantially the same procedure as Example 1, except using 5,6-diamino-1-phenyl-3-propyl-2,4 (1H, 3H)-pyrimidinedione.

TOF-MS: m/z 493 [M+H]⁺

¹H-NMR (CDCl₃): δ0.85 (3H, t, 7.2 Hz), 1.48–1.58 (m, 2H), 1.60 (3H, s), 1.90–2.04 (1H, m), 2.08 (3H, s), 2.18 (3H, s), 2.29 (3H, s), 2.30–2.38 (1H, m), 2.54–2.64 (2H, m), 3.69–3.75 (2H , m), 4.32 (1H, s), 5.17 (2H, bs), 7.27–7.36 (2H, m), 7.53–7.60 (3H, m), 8.4 (1H, b)

EXAMPLE 11

5-(6-Hydroxy-2,5,7,8-tetramethylchroman-2-carboxamido)-3-methyl-6-methylamino-1-phenyl-2,4 (1H, 3H)-pyrimidinedione The title compound was prepared by repeating substantially the same procedure as Example 1, except using 5-amino-3-methyl-6-methylamino-1-phenyl-2,4 (1H, 3H)-pyrimidinedione.

TOF-MS: m/z 479 [M+H]⁺

¹H-NMR (DMSO-d₆): δ1.46 (3H, s), 1.74–1.88 (1H, m), 2.00 (3H, s), 2.07 (3H, s), 2.12 (3H, s), 2.20–2.30 (1H, m), 2.55–2.65 (5H, m), 3.15 (3H, s), 7.25–7.35 (2H, m), 7.48–7.56 (3H, m), 8.5 (1H, b)

EXAMPLE 12

1-(4-Fluorophenyl)-6-dimethylamino-5-(6-hydroxy-2,5,7,8-tetramethylchroman-2-carboxamido) -3-methyl-2,4 (1H, 3H)-pyrimidinedione The title compound was prepared by repeating substantially the same procedure as Example 1, except using 5-amino-6-dimethylamino-1-(4-fluorophenyl)-3-methyl-2,4 (1H, 3H) -pyrimidinedione.

TOF-MS: m/z 511 [M+H]⁺

¹H-NMR (DMSO-d₆): δ1.47 (3H, s), 1.75–1.90 (1H, m), 2.01 (3H, s), 2.08 (3H, s), 2.12 (3H, s), 2.20–2.30 (1H, m), 2.37 (6H, s), 2.54–2.64 (2H, m), 3.19 (3H, s), 7.30–7.43 (4H, m), 8.5 (1H, b)

EXAMPLE 13

6-Amino-5-(6-methoxy-2,5,7,8-tetramethylchroman-2-carboxamido)-3-methyl-1-phenyl-2,4 (1H, 3H-pyrimidinedione The title compound was prepared by repeating substantially the same procedure as Example 1, except using 6-methoxy-2,5,7,8-tetramethylchroman-2-carboxylic acid.

TOF-MS: m/z 479 [M+H]⁺

¹H-NMR (CDCl₃): δ1.61 (3H, s), 1.90–2.04 (1H, m), 2.12 (3H, s), 2.21 (3H, s), 2.28 (3H, s), 2.30–2.38 (1H, m), 2.50–2.70 (2H, m), 3.35 (3H, s), 3.62 (3H, s), 5.18 (2H, bs), 7.27–7.36 (2H, m), 7.52–7.60 (3H, m), 8.42 (1H, bs)

EXAMPLE 14

5-(6-Acetoxy-2,5,7,8-tetramethylchroman-2-carboxamido)-6-amino-3-methyl-1-phenyl-2,4 (1H, 3H)-pyrimidinedione The compound of Example 1 (1.77 g, 3.80 mmol) and pyridine (0.154 mL, 1.90 mmol) were dissolved in dichloromethane (30 mL). To the resultant solution was added dropwise acetic anhydride (0.714 mL, 7.60 mmol) under ice cooling. The resultant reaction mixture was stirred overnight at room temperature, washed with 1N hydrochloric acid and 10% aqueous solution of sodium chloride successively, dried over anhydrous sodium sulfate, and concentrated under reduced pressure. The residue was suspended in ethyl acetate and filtered to give the title compound (yield 87%).

TOF-MS: m/z 507 [M+H]⁺

¹H-NMR (CDCl₃): δ1.65 (3H, s), 1.90–2.04 (1H, m), 1.93 (3H, s), 2.04 (3H, s), 2.28 (6H, s), 2.30–2.45 (1H, m), 2.50–2.70 (2H, m), 3.35 (3H, s), 4.69 (1H, b), 5.30 (1H, b), 7.26–7.35 (2H, m), 7.52–7.60 (3H, m), 7.89 (0.5H, b), 8.40 (0.5H, b)

EXAMPLE 15

6-Amino-3-methyl-1-phenyl-5-[4-(3,5,6-trimethyl-1,4-benzoquinon-2-yl)-2-hydroxy-2-methylbutyramido]-2,4 (1H, 3H)-pyrimidinedione The title compound was obtained by repeating substantially the same procedure as Example 1, except using 4-(3,5,6-trimethyl-1,4-benzoquinon-2-yl)-2-hydroxy-2-methylbutyric acid which had been prepared by oxidation of 6-hydroxy-2,5,7,8-tetramethylchroman-2-carboxylic acid with ammonium cerium (IV) nitrate (yield 62%). The title compound was found in plasma a guinea pig as one of metabolites when the compound of Example 1 was orally administered to the guinea pig.

TOF-MS: m/z 481 [M+H]⁺

¹H-NMR (CDCl₃): δ1.54 (3H, s), 1.63–1.75 (1H, m), 1.95–2.05 (1H, m), 1.97 (3H, s), 1.99 (3H, s), 2.01 (3H, s), 2.41–2.52 (1H, m), 2.63–2.73 (1H, m), 3.36 (3H, s), 4.11 (1H, s), 5.33 (2H, bs), 7.37–7.40 (2H, m), 7.52–7.63 (3H, m), 8.54 (1H, bs)

EXAMPLE 16

6-Amino-5-[4-(2,5-dihydroxy-3,4,6-trimethylphenyl)-2-hydroxy-2-methylbutyramido]-3-methyl-1-phenyl-2,4 (1H, 3H)-pyrimidinedione The compound of Example 15 (0.48 g, 1.0 mmol) was dissolved in ethanol (3 mL). The resultant solution was stirred at room temperature overnight under hydrogen atmosphere in the presence of 10% Pd/C. The catalyst in the solution was filtered off, and the filtrate was concentrated under reduced pressure to give the title compound.

ESI-MS (Electro-spray-ionization mass stectrum): m/z 483.21 [M+H]⁺

EXAMPLE 17

6-Amino-5-[(6-hydroxy-2,5,7,8-tetramethyl-2-chromanylmethyl amino]-3-methyl-1-phenyl-2,4 (1H, 3H)-pyrimidinedione The compound of Example 14 (64 mg, 1.0 mmol) was dissolved in THF (10 mL). To the resultant solution was added borane-methyl sulfide complex (10M, 0.24 mL, 2.4 mmol). The resultant reaction mixture was refluxed for 5 h. To the resultant was added 1N hydrochloric acid (2.4 mL) under ice-cooling. The resultant mixture was refluxed for 2 h, followed by concentration under reduced pressure. The residue was extracted with dichloromethane after addition of 1N aqueous solution of sodium hydroxide. The organic layer was washed with 10% aqueous solution of sodium chloride, dried over anhydrous sodium sulfate, and concentrated under reduced pressure. The residue was crystallized by addition of ethyl acetate and ether to give the title compound (yield 35%).

TOF-MS: m/z 451 [M+H]$^+$ $^1$H-NMR (CDCl$_3$): δ1.24 (3H, s), 1.65–1.80 (1H, m), 2.05 (3H, s), 2.10 (3H, s), 2.12 (3H, s), 1.95–2.20 (1H, m), 2.60–2.70 (2H, m), 3.02 (2H, bs), 3.36 (3H, s), 4.24 (1H, s), 4.78 (2H, bs), 7.25–7.35 (2H, m), 7.50–7.60 (3H, m)

EXAMPLE 18

6-Amino-5-[N-(6-hydroxy-2,5,7,8-tetramethyl-2-chromanylmethyl)aminomethyl]-3-methyl-1-phenyl-2,4 (1H, 3H)-pyrimidinedione 6-Amino-3-methyl-1-phenyl-2,4 (1H, 3H)-pyrimidinedione (5.00 g, 23 mmol) was suspended in dimethylformamide (77 mL). To the resultant suspension was added phosphorus oxychloride (2.57 mL, 27.6 mmol), and the resultant mixture was reacted at 60° C. for 3 h. The reaction mixture was diluted with water, and adjusted to ca. pH 12 with sodium hydroxide. The precipitates formed in the reaction mixture was filtered to give a crude product. The crude product was recrystallized from a mixture of ethanol, ethyl acetate and water to give an aldehyde, 6-amino-5-formyl-3-methyl-1-phenyl-2,4 (1H, 3H)-pyrimidinedione (yield 75%).

To a solution of 6-hydroxy-2,5,7,8-tetramethylchroman-2-carboxamide (1.0 g, 4.0 mmol) in THF (30 mL) was added borane-methyl sulfide complex (10M, 1.9 mL, 19 mmol). The resultant mixture was refluxed for 7 h. To the resultant reaction mixture was added 1N hydrochloric acid (9.6 mL) under ice-cooling, and the resultant mixture was further refluxed for 2 h followed by concentration under reduced pressure. The residue was extracted with ethyl acetate after addition of 1N aqueous solution of sodium hydroxide. The organic layer was washed with 10% aqueous solution of sodium chloride, dried over anhydrous sodium sulfate, concentrated under reduced pressure, and purified by silica-gel column chromatography to give an amine, 2-aminomethyl-6-hydroxy-2,5,7,8-tetramethylchroman (yield 55%).

The aldehyde (204 mg, 0.83 mol) and the amine (353 mg, 1.25 mol) thus prepared were dissolved in dichloroethane (4 mL), and the solution was heated at 70° C. for 7 h to react with one another. The resultant reaction mixture was cooled to room temperature and then sodium triacetoxyborohydride (352 mg, 1.66 mmol) was added thereto. The mixture was allowed to react at room temperature overnight. The reaction mixture was acidified with diluted hydrochloric acid, adjusted to pH 8–9 with sodium hydroxide, and then extracted with dichloromethane. The organic layer was washed with 10% aqueous solution of sodium chloride, dried over anhydrous sodium sulfate, concentrated under reduced pressure, and then crystallized from ethyl acetate/ethanol to give the title compound (yield 26%).

TOF-MS: m/z 466 [M+E]$^+$ $^1$H-NMR (DMSO-d$_6$): δ1.09 (3H, s), 1.40–1.60 (1H, m), 1.99 (3H, s), 2.03 (3H, s), 2.07 (3H, s), 1.85–2.15 (1H, m), 2.50–2.80 (4H, m), 3.12 (3H, s), 3.56 (1H, d, 12 Hz), 3.75 (1H, d, 12 Hz), 5.40 (2H, bs), 7.10–7.26 (2H, m), 7.40–7.55 (3H, m)

EXAMPLE 19

6-Amino-5-(N-butyl-6-hydroxy-2,5,7,8-tetramethylchroman-2-carboxamidomethyl)-3-methyl-1-phenyl-2,4 (1H, 3H)-pyrimidinedione Reductive amination of 6-amino-5-formyl-3-methyl-1-phenyl-2,4 (1H, 3H) -pyrimidinedione with N-butylamine was performed in substantially the same manner as Example 18 to thereby give an intermediate, 6-amino-5-(N-butylaminomethyl)-3-methyl-1-phenyl-2,4 (1H, 3H)-pyrimidinedione. The intermediate was reacted with 6-hydroxy-2,5,7,8-tetramethylchroman-2-carboxylic acid by a conventional condensation method to give the title compound (yield 36%).

$^1$H-NMR (CDCl$_3$): δ0.95 (3H, t, 7.2 Hz), 1.33 (2H, t of q, 7.2 Hz, 7.2 Hz), 1.57 (3H, s), 1.60–1.75 (3H, m), 2.03 (3H, s), 2.15 (3H, s), 2.17 (3H, s), 2.45–2.68 (3H, m), 2.45–2.65 (2H, m), 3.32 (3H, s), 3.52–3.67 (1H, m), 3.80–3.95 (1H, m), 4.28 (1H, bs), 4.41 (1H, d, 16 Hz), 4.52 (1H, d, 16 Hz), 5.85 (b), 7.13–7.32 (2H, m), 7.48–7.60 (3H, m)

Evaluation 1

Inhibition of picryl chloride-induced dermatitis

Effect of the compounds of the present invention on picryl chloride-induced dermatitis, which is a typical model of type IV allergic inflammation, was estimated by the Asherson's method [*Immunology*, 15, 405 (1968)] in the following manner.

A 7% (w/v) solution of picryl chloride in acetone (0.1 mL) was applied on a portion of the abdominal skin of each of ICR male mice to sensitize the mice. After 7 days, a 1% (w/v) solution of pioryl chloride in acetone (0.02 mL) was applied on the ears of the individual mice to induce allergic reaction. Just after the challenge, 0.04 mL of acetone (control) or a 0.25–2.5% (w/v) solution of the test compound in acetone was applied on the ear. Increase of the ear thickness of the individual mice was measured at 24 h after the challenge, and inhibitory effect of the test compound on the dermatitis was estimated based on the difference in ear thickness between before and after the induction of the allergic reaction.

The hydroquinone derivative of the present invention had inhibitory effect on swelling as exemplified below. The results show that the hydroquinone derivative of the present invention is effectively absorbed through skin and inhibits dermatitis at the diseased portion by percutaneous administration.

| Compound | Concentration (%) | Inhibition (%) |
|---|---|---|
| Example 1 | 0.25 | 69 |
| Example 2 | 0.75 | 65 |
| Example 3 | 0.75 | 69 |
| Example 11 | 0.75 | 44 |
| Example 13 | 2.50 | 33 |
| Example 14 | 0.75 | 53 |
| Example 15 | 0.75 | 70 |
| Example 17 | 0.75 | 80 |
| Example 19 | 0.25 | 49 |

Evaluation 2

Inhibition of albumin-induced asthma

Effect of the compounds of the present invention on albumin-induced asthma was estimated in the following manner.

Inhalation of 1% ovalbumin using ultrasonic nebulizer into Hartley male guinea pigs was performed 10 min/day over 8 days to sensitize the guinea pigs. One week after the last sensitization, inhalation of 2% ovalbumin was performed for 5 min. to induce allergic reaction. Metyrapone (10 mg/kg, i.v.) was adminised at 24 h and 1 h before the challenge, propylene glycol (control) or a solution of the test compound in propylene glycol was orally administered at 1 h before and 3 h after the challenge, and pyrilamine (10 mg/kg, i.p.) was intraperitoneally administered at 30 min before the challenge. Air way resistance was measured by double flow plethysmography at 1 min, 4 h, 5 h, 6 h, 7 h, and 8 h after the challenge, and inhibitory effect of the test compound on the asthma was estimated based on the measurements obtained.

As a result, the compound of Example 1 (100 mg/kg) showed 62% inhibition on the air way reaction at 1 min after the challenge, and 50% inhibition on the air way reaction (AUC) during 4–8 h after the challenge. The results show that the hydroquinone derivative of the present invention is effectively absorbed through the digestive tract and inhibits asthma by oral administration.

Formulation 1
Water soluble ointment
Water soluble ointment of the following formulation was prepared by a conventional manner.
Contents in 2 g of the ointment
The compound of Example 1 40 mg
Poly(ethylene glycol) 400 1372 mg
Poly(ethylene glycol) 4000 588 mg Formulation 2
Tablets for oral administration
Tablets of the following formulation were prepared by a conventional manner.
Contents in a tablet
the compound of example 1 100 mg
Lactose 353 mg
calboxymethylcellulose calcium 30 mg
hydroxymethylcellulose 7 mg
magnesium stearate 5 mg
crystalline cellulose 5 mg

What is claimed is:

1. A process for preparing a hydroquinone derivative represented by formula (I):

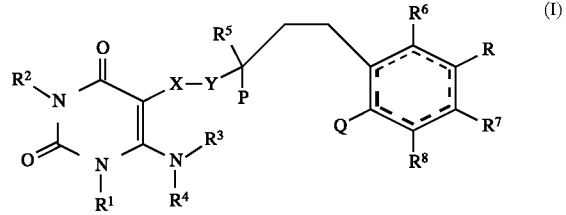

wherein:

$R^1$ is a phenyl group which is unsubstituted or substituted with a substituent or substituents each independently selected from the group consisting of a halogen atom, a C1–4 alkyl group and a C1–4 alkoxy group;

$R^2$ is a hydrogen atom or a C1–4 alkyl group;

each of $R^3$ and $R^4$ is independently a hydrogen atom or a C1–4 alkyl group;

$R^5$ is a hydrogen atom or a C1–4 alkyl group;

each of $R^6$, $R^7$ and $R^8$ is independently a hydrogen atom or a C1–4 alkyl group;

P is a hydroxyl group;

Q is a hydroxyl group, a C1–4 alkoxy group, a C1–18 acyloxy group or an oxo group;

P may form together with Q an ether bond;

R is a hydroxyl group, a C1–4 alkoxy group, a C1–18 acyloxy group or an oxo group, provided that when one of said Q and said R is an oxo group, the other is also an oxo group;

X is an —$NR^{10}$— group in which $R^{10}$ is a hydrogen atom or a C1–4 alkyl group;

Y is a carbonyl group; and dotted bonds in a six membered ring represent that said six membered ring has the maximum number of double bonds or a salt thereof, which comprises condensing a 5,6-diamino-2,4(1H, 3H)-pyrimidinedione derivative represented by formula (I'):

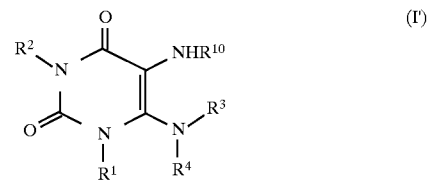

with a carboxylic acid represented by formula (I"):

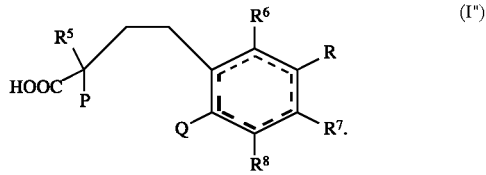

2. The process according to claim 1, wherein P forms together with Q an ether bond.

* * * * *